US011033565B2

(12) United States Patent
Manetta et al.

(10) Patent No.: US 11,033,565 B2
(45) Date of Patent: *Jun. 15, 2021

(54) TOPICAL APPLICATION OF IVERMECTIN FOR THE TREATMENT OF DERMATOLOGICAL CONDITIONS/AFFLICTIONS

(71) Applicant: GALDERMA HOLDING SA, La Tour-de-Peilz (CH)

(72) Inventors: Vincent Manetta, Bordentown, NJ (US); Gary R. Watkins, Piscataway, NJ (US)

(73) Assignee: Galderma Holding SA, La Tour-de-Peilz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,362

(22) Filed: Jun. 16, 2017

(65) Prior Publication Data
US 2017/0281664 A1 Oct. 5, 2017

Related U.S. Application Data

(63) Continuation of application No. 14/792,201, filed on Jul. 6, 2015, which is a continuation of application No. 14/337,966, filed on Jul. 22, 2014, which is a continuation of application No. 14/063,897, filed on Oct. 25, 2013, now Pat. No. 8,815,816, which is a continuation of application No. 13/851,816, filed on Mar. 27, 2013, now Pat. No. 8,598,129, which is a continuation of application No. 13/310,633, filed on Dec. 2, 2011, now Pat. No. 8,415,311, which is a continuation of application No. 12/483,604, filed on Jun. 12, 2009, now Pat. No. 8,093,219, which is a continuation of application No. 11/255,910, filed on Oct. 24, 2005, now Pat. No. 7,550,440, which is a continuation of application No. PCT/EP2004/004950, filed on Apr. 22, 2004.

(60) Provisional application No. 60/468,994, filed on May 9, 2003.

(30) Foreign Application Priority Data

Apr. 24, 2003 (FR) ...................................... 0305048

(51) Int. Cl.
*A61K 31/7048* (2006.01)
*A61K 9/107* (2006.01)
*A61K 31/35* (2006.01)
*A61K 9/00* (2006.01)

(52) U.S. Cl.
CPC ........ *A61K 31/7048* (2013.01); *A61K 9/0014* (2013.01); *A61K 9/107* (2013.01); *A61K 31/35* (2013.01)

(58) Field of Classification Search
CPC ..... A61K 31/7048; A61K 9/107; A61K 31/35
See application file for complete search history.

(56) References Cited

U.S. PATENT DOCUMENTS

| | | |
|---|---|---|
| 5,332,577 A | 7/1994 | Gertner et al. |
| 5,656,280 A | 8/1997 | Herb et al. |
| 5,952,372 A | 9/1999 | McDaniel |
| 6,013,636 A | 1/2000 | Harvey |
| 6,066,328 A | 5/2000 | Ribier et al. |
| 6,133,310 A | 10/2000 | Parks |
| 6,136,328 A | 10/2000 | Sebillotte-Arnaud et al. |
| 6,319,945 B1 | 11/2001 | Parks |
| 6,399,652 B1 | 6/2002 | Parks |
| 6,433,006 B2 | 8/2002 | Parks |
| 6,544,531 B1 | 4/2003 | Cole et al. |
| 7,550,440 B2 | 6/2009 | Manetta et al. |
| 8,093,219 B2 | 1/2012 | Manetta et al. |
| 8,415,311 B2 | 4/2013 | Manetta et al. |
| 8,470,788 B2 | 6/2013 | Manetta et al. |
| 2002/0035076 A1 | 3/2002 | Parks |
| 2002/0035161 A1 | 3/2002 | Segura et al. |
| 2002/0061855 A1 | 5/2002 | Parks |
| 2007/0116731 A1 | 5/2007 | Astruc et al. |
| 2012/0077766 A1 | 3/2012 | Manetta et al. |

FOREIGN PATENT DOCUMENTS

| | | |
|---|---|---|
| EP | 0045655 A2 | 2/1982 |
| FR | 2867684 A1 | 9/2005 |
| WO | 01/28555 A1 | 4/2001 |
| WO | 03/032976 A1 | 4/2003 |
| WO | 03/032977 A1 | 4/2003 |
| WO | 03/066009 A1 | 8/2003 |
| WO | 03/075656 A2 | 9/2003 |

(Continued)

OTHER PUBLICATIONS

"Cetaphil cleansers and moisturizers" Online! 2004, XP002287576; Retrieved from the Internet: URL:http://vvwvv.cetaphil.com/product_information/moisturizers.cfm; retrieved on Jul. 8, 2004.

(Continued)

*Primary Examiner* — Bahar Craigo
(74) *Attorney, Agent, or Firm* — Foley & Lardner LLP; Sunit Talapatra

(57) ABSTRACT

Dermatological conditions/afflictions such as rosacea, common acne, seborrheic dermatitis, perioral dermatitis, acneform rashes, transient acantholytic dermatosis, and acne necrotica miliaris, most notably rosacea, are treated by topically applying onto the affected skin area of an individual in need of such treatment, a topical pharmaceutical composition which comprises a thus effective amount of ivermectin.

36 Claims, No Drawings

(56) References Cited

FOREIGN PATENT DOCUMENTS

WO     WO 2004/093886 A1     11/2004

OTHER PUBLICATIONS

Victoria, et al., "Topical Ivermectin: A New Successful Treatment for Scabies" Pediatric Dermatology, 2001, pp. 63-65, vol. 18, No. 1.

International Search Report for corresponding PCT/EP2004/004950 dated Aug. 16, 2004 (in English).

Loo, et al., "Ivermectin cream in rosacea: comparison with metronidazole gel", British Association of Dermatologists, British Journal of Dermatology, vol. 151, 2004, p. 61.

The United States Pharmacopeia The National Formulary, Authority of the United States Pharmacopeia Convention, Inc., published Jan. 1, 1995, pp. 2226-2227.

Handbook of Pharmaceutical Excipients, Second Edition, American Pharmaceutical Association Washington, 1994, pp. 71-73, 123-125, 176-179, 243-246, 269-273, 310-313, 338, 339, 411-414, 473-476, 494-497, 534, 535, 550, 551, 556, and 557.

Gennaro, "Remington: The Science and Practice of Pharmacy", Mack Publishing Company, 1995, pp. 935, 1338-1339, 1396, 1405-1406, 1414. 1496-1497, 1509-1515, 1585-1591.

EU Clinical Trial No. 2008-002679-29, dated May 26, 2008, https://www.clinicaltrialsregister.ed/ctr-search/trial/2008-002679-29/DE, retrieved Jan. 23, 2017.

Clinical Trials Identifier: NCT01493947, updated Apr. 19, 2012, ClinicalTrials.gov archive, https://clinicaltrials.gov/archive/NCT01493947/2012_04_19, retrieved Jan. 23, 2017.

Pascoe, "More Proof that CD5024 is Ivermectin", Rosacea Support Group, Apr. 9, 2012, https://rosacea-support.org/more-proof-that-cd5024-is-ivermectin.html, retrieved Oct. 23, 2017.

Clinical Study Report No. RD.03.SRE.40064, EUDRACT No. 2008-002679-29, IND No. 76064, Study Title: Plasma Pharmacokinetics Study of CD5024 1% Cream in Subjects With Papulopustular Rosacea, 2008, 12 pages.

US 11,033,565 B2

TOPICAL APPLICATION OF IVERMECTIN FOR THE TREATMENT OF DERMATOLOGICAL CONDITIONS/AFFLICTIONS

CROSS-REFERENCE TO RELATED APPLICATIONS

This application is a continuation of earlier copending U.S. patent application Ser. No. 14/792,201, filed Jul. 6, 2015, which is a continuation of U.S. patent application Ser. No. 14/337,966, filed Jul. 22, 2014, which is a continuation of U.S. patent application Ser. No. 14/063,897, filed Oct. 25, 2013, now U.S. Pat. No. 8,815,816, which is a continuation of U.S. patent application Ser. No. 13/851,816, filed Mar. 27, 2013, now U.S. Pat. No. 8,598,129, which is a continuation of U.S. patent application Ser. No. 13/310,633, filed Dec. 2, 2011, now U.S. Pat. No. 8,415,311, which is a continuation of U.S. patent application Ser. No. 12/483,604, filed Jun. 12, 2009, now U.S. Pat. No. 8,093,219, which is a continuation of U.S. patent application Ser. No. 11/255,910, filed Oct. 24, 2005, now U.S. Pat. No. 7,550,440, which is a continuation of International Application No. PCT/EP2004/004950, filed Apr. 22, 2004 and designating the United States (published in the English language on Nov. 4, 2004 as WO 2004/093886 A1), which claims benefit of U.S. Provisional Application No. 60/468,994, filed May 9, 2003, and also claims priority under 35 U.S.C. § 119 of Application No. 03/05048, filed in France on Apr. 24, 2003, each earlier application hereby expressly incorporated by reference herein and each assigned to the assignee hereof.

BACKGROUND OF THE INVENTION

Technical Field of the Invention

The present invention relates to the formulation of ivermectin into topical pharmaceutical compositions useful for the treatment of rosacea. This invention also relates to topical pharmaceutical compositions suited for administration to humans, comprising ivermectin.

Description of Background and/or Related and/or Prior Art

Ivermectin is a mixture of two compounds belonging to the avermectin class, 5-O-demethyl-22,23-dihydroavermectin $A_{1a}$ and 5-O-demethyl-22,23-dihydroavermectin $A_{1b}$. They are also known as 22,23-dihydroavermectin $B_{1a}$ and 22-23-dihydroavermectin $B_{1b}$. Ivermectin contains at least 80% of 22,23-dihydroavermectin $B_{1a}$ and less than 20% of 22,23-dihydroavermectin $B_{1b}$. This active agent is part of the avermectin class, a group of macrocyclic lactones produced by the bacterium Streptomyces avermitilis (Reynolds J E F (Ed) (1993) Martindale). The extra pharmacopoeia, 29$^{th}$ Edition, Pharmaceutical Press, London).

In the middle of the 1980s, ivermectin was presented as a broad-spectrum anti-parasitic medicinal product for veterinary use (W. C. CAMPBELL, et al., (1983). Ivermectin: a potent new anti-parasitic agent, Science, 221, 823-828). It is effective against most common intestinal worms (except tapeworms), most acarids and some lice. It in particular exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependent chloride channels, such as those involving the neuromediator GABA (gamma-aminobutyric acid).

Ivermectin is more particularly an anthelmintic. It has already been described in humans in the treatment of river blindness caused by Onchocerca volvulus, of gastrointestinal strongyloidiasis (anguillulosis) (product Stromectol®), and of human scabies (Meinking T L et al., N. Engl. J. Med., 1995 Jul. 6; 333(1):26-30, "The treatment of scabies with ivermectin") and also in the treatment of microfilaraemia diagnoses or suspected in individuals suffering from lymphatic filariasis due to Wuchereria bancrofti.

U.S. Pat. No. 6,133,310 discloses the use of ivermectin topically in the form of a prototype of a lotion consisting of a mixture of ivermectin and water, and also mentions the possibility of a prototype of a cream consisting, for its part, of a mixture of ivermectin and an excipient such as propylene glycol or sodium lauryl sulfate, but describes no pharmaceutical composition as such. These mixtures are similar to experimental preparations used in the context of initial results of proof of concept. In fact, the elements disclosed in that patent provide no teaching to those skilled in the art regarding the feasibility of industrially acceptable pharmaceutical compositions containing ivermectin, in particular having good cosmetic properties and a shelf-life which is sufficiently long for an industrial pharmaceutical product (minimum of 2 years).

SUMMARY OF THE INVENTION

Despite the fact that all these uses in humans are limited to oral administration or to the use of experimental preparations, topical pharmaceutical compositions have now been developed suited for the treatment of humans, containing ivermectin. In addition, it has now been found that the compositions according to the invention exhibit very good stability, in particular at different pHs, and good tolerance on the skin. In fact, it has now been found that same are particularly suitable for the treatment of dermatological conditions, and more particularly well suited for the treatment of rosacea.

The present invention also features the formulation of ivermectin into topical pharmaceutical compositions useful for the treatment of rosacea, topical pharmaceutical compositions suited for human administration, comprising ivermectin, and the use of these topical pharmaceutical compositions for the treatment of rosacea (whether regime or regimen).

DETAILED DESCRIPTION OF BEST MODE AND SPECIFIC/PREFERRED EMBODIMENTS OF THE INVENTION

The ivermectin according to the invention contains at least 80% of 22,23-dihydroavermectin $B_{1a}$ and less than 20% of 22,23-dihydroavermectin $B_{1b}$.

The pharmaceutical compositions according to the invention are suited for treating the skin and may be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases. They may also be in the form of suspensions of microspheres or nanospheres or of lipid or polymeric vesicles or of polymeric patches and of hydrogels for controlled release.

These compositions for topical application may be in anhydrous form, in aqueous form of in the form of an emulsion.

In a preferred embodiment of the invention, the pharmaceutical compositions according to the invention are in the form of an emulsion of the cream or lotion type, of a gel, or of a solution.

More preferably, the compositions according to the invention are in the form of an emulsion.

Conventional emulsions as described in the prior art are unstable virtually homogeneous systems of two immiscible liquids, one of which is dispersed in the other in the form of fine droplets (micelles). This dispersion is stabilized by virtue of the action of surfactant-emulsifiers which modify the structure and the ratio of the forces at the interface, and therefore increase the stability of the dispersion by decreasing the interface tension energy.

Surfactant-emulsifiers are amphiphilic compounds which possess a hydrophobic component having affinity for oil and a hydrophilic component having affinity for water, thus creating a link between the two phases. Ionic or nonionic emulsifiers therefore stabilize oil/water emulsions by adsorbing to the interface and forming lamellar layers of liquid crystals.

The emulsifier power of nonionic surfactants is closely linked to the polarity of the molecule. This polarity is defined by the HLB (hydrophilic/lipophilic balance). Conventional emulsions are generally stabilized by a mixture of surfactants, the HLBs of which can be quite different but the proportion of which in the mixture corresponds to the required HLB of the fatty phase to be emulsified.

The compositions according to the invention will contain this type of ingredient.

The compositions according to the invention are described as stable emulsions in that they exhibit good physical and chemical stability over time, even at a temperature above ambient temperature (for example 45-55° C.), as shown in the examples described hereinafter.

The ivermectin in the compositions according to the invention also, surprisingly, exhibits good chemical stability in the case of pH variation.

The compositions according to the invention are advantageously emulsions which comprise:
  a) an oily phase comprising fatty substances;
  b) at least one surfactant-emulsifier;
  c) ivermectin;
  d) one or more solvent(s) and/or propenetrating agent(s) for the active agent;
  e) and water.

More particularly, the compositions according to the invention are emulsions which comprise:
  a) an oily phase comprising fatty substances;
  b) at least one surfactant-emulsifier;
  c) ivermectin;
  d) one or more solvent(s) and/or propenetrating agent(s) for the active agent;
  e) one or more gelling agent(s);
  f) and water.

The oily phase of the composition according to the invention may comprise, for example, vegetable, mineral, animal or synthetic oils, silicone oils, Guerbet alcohols or other substances, and mixtures thereof.

As an example of a mineral oil, mention may be made, for example, of paraffin oils of various viscosities, such as Primol 352, Marcol 82 or Marcol 152 marketed by Esso.

As a vegetable oil, mention may be made of sweet almond oil, palm oil, soybean oil, sesame oil and sunflower oil.

As an animal oil, mention may be made of lanolin, squalene, fish oil and mink oil.

As a synthetic oil, mention may be made of esters, such as cetearyl isononanoate marketed in particular under the name Cetiol SN by Cognis France, diisopropyl adipate, for instance the product marketed under the name Ceraphyl 230 by ISF, isopropyl palmitate, for instance the product marketed under the name Crodamol IPP by Croda, or caprylic capric triglyceride such as Miglyol 812 marketed by Huls/Lambert Rivière.

As a silicone oil, mention may be made of a dimethicone, such as the product marketed under the name Dow Corning 200 fluid, or a cyclomethicone, such as the product marketed under the name Dow Corning 244 fluid by Dow Corning, or the product marketed under the name Mirasil CM5 by SACI-CFPA.

As other fatty substances, mention may be made of fatty acids such as stearic acid, fatty alcohols such as stearyl alcohol, cetostearyl alcohol and cetyl alcohol, or derivatives thereof, waxes such as beeswax, carnauba wax or candelilla wax, and also gums, in particular silicone gums.

The ingredients of the oily phase may be selected in a varied manner by those skilled in the art in order to prepare a composition having the desired properties, for example of consistency or of texture.

The oily phase of the composition according to the invention preferably comprises a synthetic oil and/or a silicone oil; as synthetic oil, isopropyl palmitate such as the product marketed under the name Crodamol IPP by Croda or isopropyl myristate such as the product marketed under the name Crodamol IPM by Croda is preferred; as silicone oil, a dimethicone is preferred.

The oily phase of the emulsion according to the invention may be present at a content of from 3 to 50% by weight relative to the total weight of the composition, and preferably from 6 to 20% by weight.

The compositions according to the invention contain surfactant-emulsifiers. Among these compounds, mention may be made, by way of examples, of the glyceryl/PEG 100 stearate marketed under the name Arlacel 165FL by UNIQEMA or under the name Simulsol 165 by SEPPIC; polyoxyethylenated fatty acid esters such as Arlatone 983 from the company UNIQEMA or the polyoxyethylenated (2) stearyl alcohol marketed under the name Brij72 combined with the polyethylenated (21) stearyl alcohol marketed under the name Brij721 by UNIQEMA; sorbitan esters such as the sorbitan oleate marketed under the name Arlacel 80 by ICI or marketed under the name Crill 4 by Croda, the sorbitan sesquioleate marketed under the name Arlacel 83 by ICI or marketed under the name Montane 83 by SEPPIC, or else sorbitan isostearate; fatty alcohol ethers.

The compositions according to the invention advantageously comprise up to 15% by weight of suitable surfactant-emulsifier, preferably from 2 to 12% by weight, and more particularly from 2 to 6% by weight, relative to the total weight of the composition.

The compositions according to the invention comprise from 0.001 to 10% of ivermectin by weight relative to the total weight of the composition. Preferably, the compositions according to the invention contain from 0.1 to 5% of ivermectin by weight relative to the total weight of the composition.

By way of example of a solvent and/or propenetrating agent for the ivermectin active agent, mention will preferably be made of propylene glycol, alcohols such as ethanol, isopropanol, butanol, N-methyl-2-pyrrolidone or DMSO, polysorbate 80, phenoxyethanol, and mixtures thereof.

The table below illustrates the solubility of ivermectin in various solvents:

| Solvents | Maximum % solubility of ivermectin in the solvent concerned (weight/weight) |
| --- | --- |
| Triacetin | 7.22 |
| Propylene glycol | 21.83 |
| N-methyl-2-pyrrolidone | 58.13 |
| Propylene glycol/oleyl alcohol (4 parts/2 parts) | 27.31 |

The compositions of the invention contain from 0.1 to 20%, and preferably from 1 to 10%, of a solvent and/or propenetrating agent for the ivermectin active agent.

The compositions according to the invention may also comprise aqueous phase gelling compounds ranging from 0.01 to 5% by weight relative to the total weight of the composition. Among the gelling agents which can be used in the composition according to the invention, mention may be made of carboxyvinyl polymers (carbomers) and, by way of non-limiting examples, of carbomer, Carbopol 981, Carbopol ETD 2020, Carbopol 980, Carbopol Ultrez 10 NF and Pemulen TR1, marketed by NOVEON.

As aqueous phase gelling agents, mention may also be made of cellulose derivatives such as, for example, hydroxypropylmethylcellulose or hydroxyethylcellulose; xanthan gums, aluminum/magnesium silicates such as Veegum K or Veegum Ultra remarketed by Vanderbilt, guar gums and the like, polyacrylamides such as the mixture polyacrylamide/C13-14 isoparaffin/laureth-7, for instance that marketed, for example, by SEPPIC under the name Sepigel 305, or the mixture acrylamide, AMPS copolymer dispersion 40%/isohexadecane under the name Simulgel 600PHA, or the family of modified starches such as Structure Solanace remarketed by National Starch, or mixtures thereof.

The compositions of the invention preferentially contain from 0.01 to 5%, and preferably from 0.1 to 3%, of gelling agent.

As gelling agent according to the invention, use will preferably be made of carbomers, and preferably Pemulen TR1 or aluminum/magnesium silicas such as Veegum K.

The compositions of the invention also contain water ranging from 30 to 95%, and preferably from 60 to 80%, by weight relative to the total weight of the composition. The water used in the composition according to the invention will preferably be purified water.

The pharmaceutical compositions according to the invention may also contain inert additives or combinations of these additives, such as
flavor enhancers;
preservatives;
stabilizers;
humidity regulators;
pH regulators;
osmotic pressure modifiers;
UV-A and UV-B screening agents;
and antioxidants.

Of course, one skilled in this art will take care to choose the optional compound(s) to be added to these compositions in such a way that the advantageous properties intrinsically associated with the present invention are not, or are not substantially, altered by the envisaged addition.

These additives may be present in the composition at from 0.001 to 20% by weight relative to the total weight of the composition.

The compositions according to the invention are advantageously emulsions which comprise:
a) 6 to 20% of an oily phase;
b) 2 to 12% of a surfactant-emulsifier;
c) 0.1 to 5% of ivermectin;
d) 0.1 to 20% of solvent;
e) 0.01 to 5% of gelling agents;
f) and water.

The pH will preferably range from 6.0 and 6.5. Verification of the natural pH of the mixture and possible correction with a solution of a neutralizing agent, and also the incorporation of the optional additives, may be carried out, according to their chemical nature, during one of the steps of the method of preparation, described above.

Examples of compositions according to the present invention are illustrated in Examples 1 to 6 to follow.

The present invention also features topical compositions suited for human use, characterized in that they are emulsions comprising:
a) an oily phase comprising fatty substances;
b) at least one surfactant-emulsifier;
c) ivermectin;
d) one or more solvent(s) and/or propenetrating agent(s) for the active agent;
e) and water.

More particularly, this composition may comprise:
a) an oily phase comprising fatty substances;
b) at least one surfactant-emulsifier;
c) ivermectin;
d) one or more solvent(s) and/or propenetrating agent(s) for the active agent;
e) one or more gelling agent(s);
f) and water.

Preferably, the composition comprises:
a) 6 to 20% of an oily phase;
b) 2 to 12% of a surfactant-emulsifier;
c) 0.1 to 5% of ivermectin;
d) 0.1 to 20% of solvent;
e) 0.01 to 5% of gelling agents;
f) and water.

The ingredients being as defined above.

This invention also features formulation of the compositions according to the invention into pharmaceutical preparations useful to treat dermatological conditions/afflictions.

The formulation of ivermectin into topical pharmaceutical compositions for human use according to the invention is particularly useful for the treatment of rosacea, of common acne, of seborrhoeic dermatitis, of perioral dermatitis, of acneform rashes, of transient acantholytic dermatosis, and of acne necrotica miliaris.

The formulation of ivermectin into topical pharmaceutical compositions for human use according to the invention is more particularly useful in a regime or regimen for the treatment of rosacea.

In order to further illustrate the present invention and the advantages thereof, the following specific examples of compositions comprising ivermectin and the stability and tolerance thereof are given, it being understood that same are intended only as illustrative and in nowise limitative. In said examples to follow, all parts and percentages are given by weight, unless otherwise indicated.

Example 1: Composition 1

The Compositions of Examples 1 to 4 are Formulated According to the Following Procedure:

In a first suitable container, weigh the aqueous phase, mix at 700 rpm and heat to 65°–70° C.

In a second suitable container, weigh the oily phase, mix at 425-475 rpm and heat to 70°–75° C.

In a third suitable container, weigh the active phase and heat to 60-65° C.

Where the oily and aqueous phases are at 70° C., mix the two phases with Rayneri stirring at 900 rpm until complete homogeneity, and then cool.

Allow the emulsion to cool to 55-60° C., add the active phase with stirring at 600 rpm. Decrease, at 600 rpm, to 30° C.

Adjust the pH to 6.0.

| Ingredients | % by weight relative to the total weight of the composition |
|---|---|
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 2.5 |
| Steareth-20 | 3.0 |
| Sorbitan stearate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 2: Composition 2

| Ingredients | % by weight relative to the total weight of the composition |
|---|---|
| Ivermectin | 1.00 |
| Glycerol | 4.0 |
| Steareth-2 | 1.0 |
| Steareth-21 | 2.0 |
| Aluminum magnesium silicate/titanium dioxide/silica | 1.0 |
| Methyl para-hydroxybenzoate | 0.2 |
| Propyl para-hydroxybenzoate | 0.1 |
| Disodium EDTA | 0.05 |
| Citric acid monohydrate | 0.05 |
| Isopropyl palmitate | 4.0 |
| Glyceryl/PEG 100 stearate | 2.0 |
| Self-emulsifiable wax | 1.0 |
| Palmitostearic acid | 2.00 |
| Dimethicone 200-350 cS | 0.5 |
| Propylene glycol | 4.0 |
| Glyceryl triacetate | 1.00 |
| Phenoxyethanol | 0.5 |
| 10% sodium hydroxide | qs pH |
| Water | qs 100 |

Example 3: Composition 3

| Ingredients | % by weight relative to the total weight of the composition |
|---|---|
| Ivermectin | 1.00 |
| Glycerol | 4.0 |
| Acrylate C10-30 alkyl acrylate crosspolymer | 0.15 |
| Methyl para-hydroxybenzoate | 0.2 |
| Disodium EDTA | 0.05 |
| Citric acid monohydrate | 0.05 |
| Isopropyl myristate | 4.0 |
| Cetyl alcohol | 3.0 |
| Stearyl alcohol | 2.0 |
| Self-emulsifiable wax | 0.8 |
| Palmitostearic acid | 0.5 |
| Steareth-20 | 2.0 |
| Sorbitan palmitate | 1.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 4: Composition 4

| Ingredients | % by weight relative to the total weight of the composition |
|---|---|
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 3.0 |
| Steareth-20 | 3.0 |
| Sorbitan palmitate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 5: Composition 5

The Compositions of Examples 5 and 6 are Formulated According to the Following Procedure:

Aqueous Phase:

In a first beaker, disperse the acrylate/c10-30 alkyl acrylate crosspolymer in water with Rayneri stirring at 800 rpm until a homogeneous gel is obtained. Begin heating up to 65° C.-70° C., and then add the glycerol and the additives.

Oily Phase:

In a second beaker, incorporate the constituents of the oily phase and heat up to 70° C.-75° C., homogenize with Rayneri stirring at 400 rpm.

Active Phase:

In a third beaker, weigh the constituents of the active phase (solvent+additives).

Homogenize at approximately 500 rpm and introduce a magnetic bar.

Weigh the ivermectin in a weighing boat and then introduce it into the beaker container the active phase.

Place this beaker on a magnetic stirrer until the ivermectin has dissolved.

When the oily and aqueous phases are at 70° C., mix the two phases with Rayneri stirring at 900 rpm for 10 min.

Allow the emulsion to cool to 40° C., add the active phase with Rayneri stirring at 800 rpm for 10 minutes. Decrease at 700 rpm to 30° C.

Make up the volume with a sufficient quantity of water and adjust the pH to 6.3+/−0.3.

| Ingredients | % by weight relative to the total weight of the composition |
|---|---|
| Ivermectin | 1.00 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 6: Composition 6

| Ingredients | % by weight relative to the total weight of the composition |
|---|---|
| Ivermectin | 1.4 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 7: Example of Stability of the Compositions Described in Examples 5 and 6

Assaying of the active agent by external calibration by HPLC.

| Composition tested | % of ivermectin in the composition at time t (in weeks) | | | |
|---|---|---|---|---|
| | 0 | 4 | 8 | 12 |
| Composition 5 | 100.2% | 99.6% | 100.7% | 101.3% |
| Composition 6 | 95.6% | 97% | 97.7% | 95.8% |

The results are expressed as % recovery relative to the theoretical value, and demonstrate the very good chemical stability of the ivermectin in the composition as a function of time.

Example 8: Measurement of the Chemical Stability of Ivermectin as a Function of pH in the Composition of Example 5

| T0 | | T1 month | | T2 months | |
|---|---|---|---|---|---|
| pH | % of active agent | pH | % of active agent | pH | % of active agent |
| 4.0 | 105.7 | 4.36 | 106.5 | 4.34 | 102.3 |
| 5.02 | 109.3 | 5.14 | 104.2 | 5.14 | 97.3 |
| 6.28 | 107.6 | 6.2 | 104.1 | 6.18 | 102.1 |

These results show the very good chemical stability of ivermectin in the composition as a function of pH.

Example 9: Study of Tolerance and of Acceptability of the Composition of Example 5

A randomized single-blind intra-individual study was carried out on 15 individuals with skin tending to be affected by rosacea. The composition of Example 5 was tested in comparison with a gel and with an emulsion having compositions different from the compositions according to the invention.

The individuals presented themselves three times in order to perform the various applications. In the course of each of the visits, 2 of the three products were applied so as to cover each half-face. Each product was tested twice during the study. After application and at each visit, the individuals filled in, for each product tested, a questionnaire for evaluating the clinical tolerance and the cosmetic acceptability.

The following clinical tolerance parameters were evaluated: stinging sensation, burning, dry skin, tightness or itching.

The following cosmetic acceptability parameters were evaluated: creaminess, texture, lack of a sensation of greasy and sticky skin, nourishing nature, feeling of comfort and of softness to the touch.

For all the tolerance parameters, the composition according to the invention was judged to be well tolerated by the individuals, to the same extent as the two other compositions.

In general, for all the acceptability parameters, the individuals gave their approval (good or excellent), with respect to the parameters, regarding the composition of the Example 5 in 76.66% of the cases where it was tested. This formulation therefore tends to distinguish itself from the gel-cream composition, having a 66.66% approval, and from the other emulsion, having a 63.32% approval.

Example 10: Study of Irritation Over 21 Days

A study of irritation over 21 days was carried out in order to test the irritation induced by the three compositions tested in the preceding example. No product was considered to be irritant under the conditions tested.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed:

1. A topically applicable, stable pharmaceutical emulsion, comprising, by weight relative to the total weight of the emulsion:
   1% of ivermectin;
   6 to 20% of an oily phase comprising fatty substances;
   2 to 12% of at least one surfactant-emulsifier selected from polyoxyethylenated fatty acid esters and sorbitan esters;
   0.1 to 20% of a mixture of solvents and/or propenetrating agents for the ivermectin selected from propylene glycol, ethanol, isopropanol, butanol, N-methyl-2-pyrrolidone, DMSO, polysorbate 80, phenoxyethanol, glyceryl triacetate, and oleyl alcohol;
   0.01 to 5% of one or more gelling agents, but excluding aluminum magnesium silicate/titanium dioxide/silica; and
   30% to 95% of water;
   wherein the ivermectin is chemically stable in the emulsion over a period of 8 weeks.

2. The emulsion as defined by claim 1, wherein the oily phase comprises dimethicone, cyclomethicone, isopropyl palmitate, isopropyl myristate, or mixtures thereof.

3. The emulsion as defined by claim 2, wherein the fatty substances are selected from cetostearyl alcohol, cetyl alcohol, stearyl alcohol, stearic acid, palmitostearic acid, and a self-emulsifiable wax.

4. The emulsion as defined by claim 1, wherein the sorbitan esters are selected from sorbitan monostearate, sorbitan palmitate, sorbitan oleate, sorbitan sesquioleate, and sorbitan isostearate; and the polyoxyethylenated fatty acid esters are selected from steareth-20, steareth-2, steareth-21, and ceteareth-20.

5. The emulsion as defined by claim 4, wherein the at least one surfactant-emulsifier is present in an amount of from 2% to 6% by weight relative to the total weight of the emulsion.

6. The emulsion as defined by claim 1, wherein the one or more gelling agents are selected from carbomers, cellulose derivatives, xanthan gums, guar gums, polyacrylamides, modified starches, and aluminum magnesium silicates.

7. The emulsion as defined by claim 6, wherein the one or more gelling agents are present in the emulsion in an amount of from 0.1% to 3% by weight relative to the total weight of the emulsion.

8. The emulsion as defined by claim 1, wherein the emulsion is chemically stable over a period of 12 weeks.

9. The emulsion as defined by claim 1, wherein the mixture of solvents and/or propenetrating agents are present in an amount of from 1% to 10% by weight relative to the total weight of the emulsion.

10. The emulsion as defined by claim 1, wherein the ivermectin is chemically stable in the emulsion over a period of two months at a pH of about 4.

11. The emulsion as defined by claim 1, wherein the ivermectin is chemically stable in the emulsion over a period of two months at a pH of about 5.

12. The emulsion as defined by claim 1, wherein the ivermectin is chemically stable in the emulsion over a period of two months at a pH of about 6.

13. The emulsion as defined by claim 1, wherein the water is from 60% to 80% by weight relative to the total weight of the emulsion.

14. The emulsion as defined by claim 1, wherein the emulsion has lamellar layers of liquid crystals.

15. A topically applicable, stable pharmaceutical emulsion, comprising, by weight relative to the total weight of the emulsion:
   0.001% to 1.4% of ivermectin;
   6 to 20% of an oily phase comprising fatty substances;
   2 to 12% of at least one surfactant-emulsifier selected from polyoxyethylenated fatty acid esters and sorbitan esters;
   0.1 to 20% of a mixture of solvents and/or propenetrating agents for the ivermectin selected from propylene glycol, ethanol, isopropanol, butanol, N-methyl-2-pyrrolidone, DMSO, polysorbate 80, phenoxyethanol, glyceryl triacetate, and oleyl alcohol;
   0.01 to 5% of one or more gelling agents, but excluding aluminum magnesium silicate/titanium dioxide/silica; and
   30% to 95% of water;
   wherein the ivermectin is chemically stable in the emulsion over a period of 8 weeks.

16. The emulsion as defined by claim 15, wherein the oily phase comprises dimethicone, cyclomethicone, isopropyl palmitate, isopropyl myristate, or mixtures thereof.

17. The emulsion as defined by claim 16, wherein the fatty substance is selected from cetostearyl alcohol, cetyl alcohol, stearyl alcohol, stearic acid, palmitostearic acid, and a self-emulsifiable wax.

18. The emulsion as defined by claim 15, wherein the sorbitan esters are selected from sorbitan monostearate, sorbitan palmitate, sorbitan oleate, sorbitan sesquioleate, and sorbitan isostearate; and the polyoxyethylenated fatty acid esters are selected from steareth-20, steareth-2, steareth-21, and ceteareth-20.

19. The emulsion as defined by claim 18, wherein the at least one surfactant-emulsifier is present in an amount of from 2% to 6% by weight relative to the total weight of the emulsion.

20. The emulsion as defined by claim 15, wherein the one or more gelling agents are selected from carbomers, cellulose derivatives, xanthan gums, guar gums, polyacrylamides, modified starches, and aluminum magnesium silicates.

21. The emulsion as defined by claim 20, wherein the one or more gelling agents is present in the emulsion in an amount of from 0.01% to 5% 0.1% to 3% by weight relative to the total weight of the emulsion.

22. The emulsion as defined by claim 15, wherein the emulsion is chemically stable over a period of 12 weeks.

23. The emulsion as defined by claim 15, wherein the mixture of solvent and/or propenetrating agent is present in an amount of from 1% to 10% by weight relative to the total weight of the emulsion.

24. The emulsion as defined by claim 15, wherein the ivermectin is chemically stable in the emulsion over a period of two months at a pH of about 4.

25. The emulsion as defined by claim 15, wherein the ivermectin is chemically stable in the emulsion over a period of two months at a pH of about 5.

26. The emulsion as defined by claim 15, wherein the ivermectin is chemically stable in the emulsion over a period of two months at a pH of about 6.

27. The emulsion as defined by claim 15, wherein the water is from 60% to 80% by weight relative to the total weight of the emulsion.

28. The emulsion as defined by claim 15, wherein the emulsion has lamellar layers of liquid crystals.

29. A topically applicable, stable pharmaceutical emulsion, comprising, by weight relative to the total weight of the emulsion:
    1% of ivermectin;
    6 to 20% of an oily phase comprising fatty substances;
    2 to 12 at least one surfactant-emulsifier selected from polyoxyethylenated fatty acid esters and sorbitan esters;
    0.1 to 20% of at least two of the following solvents and/or propenetrating agents for the ivermectin: propylene glycol, ethanol, isopropanol, butanol, N-methyl-2-pyrrolidone, DMSO, polysorbate 80, phenoxyethanol, glyceryl triacetate, and oleyl alcohol;
    0.01 to 5% of one or more gelling agents, but excluding aluminum magnesium silicate/titanium dioxide/silica; and
    30% to 95% of water;
    wherein the ivermectin is chemically stable in the emulsion over a period of 8 weeks.

30. The emulsion as defined by claim 29, wherein the oily phase comprises dimethicone, cyclomethicone, isopropyl palmitate, isopropyl myristate, or mixtures thereof.

31. The emulsion as defined by claim 28, wherein the fatty substances are selected from cetostearyl alcohol, cetyl alcohol, stearyl alcohol, stearic acid, palmitostearic acid, and a self-emulsifiable wax.

32. The emulsion as defined by claim 29, wherein the sorbitan esters are selected from sorbitan monostearate, sorbitan palmitate, sorbitan oleate, sorbitan sesquioleate, and sorbitan isostearate; and the polyoxyethylenated fatty acid esters are selected from steareth-20, steareth-2, steareth-21, and ceteareth-20.

33. A topically applicable, stable pharmaceutical emulsion, comprising, by weight relative to the total weight of the emulsion:
    0.001% to 1.4% of ivermectin;
    6 to 20% of an oily phase comprising fatty substances;
    2 to 12% of at least one surfactant-emulsifier selected from polyoxyethylenated fatty acid esters and sorbitan esters;
    0.1 to 20% of at least two of the following solvents and/or propenetrating agents for the ivermectin: propylene glycol, ethanol, isopropanol, butanol, N-methyl-2-pyrrolidone, DMSO, polysorbate 80, phenoxyethanol, glyceryl triacetate, and oleyl alcohol;
    0.01 to 5% of one or more gelling agents, but excluding aluminum magnesium silicate/titanium dioxide/silica; and
    30% to 95% of water;
    wherein the ivermectin is chemically stable in the emulsion over a period of 8 weeks.

34. The emulsion as defined by claim 33, wherein the oily phase comprises dimethicone, cyclomethicone, isopropyl palmitate, isopropyl myristate, or mixtures thereof.

35. The emulsion as defined by claim 34, wherein the fatty substances are selected from cetostearyl alcohol, cetyl alcohol, stearyl alcohol, stearic acid, palmitostearic acid, and a self-emulsifiable wax.

36. The emulsion as defined by claim 33, wherein the sorbitan esters are selected from sorbitan monostearate, sorbitan palmitate, sorbitan oleate, sorbitan sesquioleate, and sorbitan isostearate; and the polyoxyethylenated fatty acid esters are selected from steareth-20, steareth-2, steareth-21, and ceteareth-20.

* * * * *